| United States Patent [19] | [11] Patent Number: 4,639,365 |
| Sherry | [45] Date of Patent: Jan. 27, 1987 |

[54] GADOLINIUM CHELATES AS NMR CONTRAST AGENTS

[75] Inventor: A. Dean Sherry, Richardson, Tex.

[73] Assignee: The Board of Regents, The University of Texas System, Austin, Tex.

[21] Appl. No.: 662,075

[22] Filed: Oct. 18, 1984

[51] Int. Cl.⁴ .................. A61K 49/00; G01N 31/00; A61B 6/00

[52] U.S. Cl. ..................................... 424/9; 128/653; 128/654; 436/173; 436/806

[58] Field of Search ............... 128/653, 654; 436/173, 436/806; 424/9

[56] References Cited

U.S. PATENT DOCUMENTS

| | | | |
|---|---|---|---|
| 3,930,867 | 1/1976 | Bigelow | 96/107 |
| 3,932,451 | 1/1976 | Bigelow | 260/309.6 |
| 3,987,128 | 10/1976 | Richman | 260/936 |
| 3,996,276 | 12/1976 | Atkins | 260/551 P |
| 4,038,312 | 7/1977 | Atkins | 260/551 P |
| 4,085,106 | 4/1978 | Atkins | 260/256.4 F |
| 4,130,715 | 12/1978 | Atkins | 548/324 |
| 4,337,154 | 6/1982 | Fukuchi | 210/490 |
| 4,352,751 | 10/1982 | Wieder | 260/112 R |
| 4,374,360 | 2/1983 | Sepponen | 324/309 |
| 4,398,148 | 8/1983 | Barjhoux | 324/307 |
| 4,409,550 | 10/1983 | Fossel | 324/300 |
| 4,421,671 | 12/1983 | Cuasno | 252/310.4 F |
| 4,425,547 | 1/1984 | Sugimoto | 324/318 |
| 4,432,907 | 2/1984 | Wieder | 260/429.2 |
| 4,442,404 | 4/1984 | Bergmann | 324/309 |
| 4,450,408 | 5/1984 | Tiemann | 324/318 |
| 4,472,509 | 9/1984 | Ganson et al. | 436/811 |

FOREIGN PATENT DOCUMENTS

| | | |
|---|---|---|
| 3129906 | 2/1983 | Fed. Rep. of Germany . |
| 3401052 | 7/1984 | Fed. Rep. of Germany . |
| 2539996 | 8/1984 | France . |
| 2137612 | 10/1984 | United Kingdom . |

OTHER PUBLICATIONS

Desreux, J. F., "Nuclear Magnetic Resonance Spectroscopy of Lanthanide Complexes with a Tetraacetic Tetraaza Macrocycle, Unusual Conformation Properties," American Chemical Society, 1980, 19, 1319–1324.

Bryden, Charles C.; Reilley, Charles N.; Desreux, Jean F., "Multinuclear NMR Study of Three Aqueous Lanthanide Shift Reagents: Complexes with EDTA and Two Macrocyclic Ligands," American Chemical Society, vol. 97, 1982–Chem. Substance Index, Part 2 of 4, p. 6773; Part 4 of 4, p. 2840; Chemical Abstracts, pp. 616–617.

Weinmann, Hanns–Joachim, "Characteristics of Gadolinium—DTPA Complex: A Potential NMR Contrast Agent"; AJR 142:619–624, Mar. 1984.

Brasch, Robert C., et al., "Contrast–Enhanced NMR Imaging: Animal Studies Using Gadolinium DTPA Complex"; AJR 142:625–630, Mar. 1984.

Chen, Chi–wan, et al., "Paramagnetic Metalloporphyrins as Potential Contrast Agents in NMR Imaging", Federation of European Biochemical Societies, 1984, vol. 168, No. 1, pp. 70–74.

White, D. W., et al., "A Tris(Dialkylamino)Phosphine with Pyramidal Nitrogens", Journal of the American Chemical Society, 101:17, Aug. 1979, pp. 4921–4925.

*Primary Examiner*—Christine M. Nucker
*Assistant Examiner*—Stephen C. Wieder
*Attorney, Agent, or Firm*—Arnold, White & Durkee

[57] ABSTRACT

Chelates of gadolinium with 1,4,7-triazacyclononane-N,N',N''-triacetate; 1,4,7,10-tetrazacyclododecane-N,N',N''',tetraacetate; and 1,5,9-triazacyclododecane-N,N',N''-triacetate are useful as NMR contrast agents.

4 Claims, No Drawings

GADOLINIUM CHELATES AS NMR CONTRAST AGENTS

BACKGROUND OF THE INVENTION

The present invention relates to NMR imaging of living subjects. More specifically, it relates to agents which can be used to enhance NMR contrast in such subjects.

Nuclear magnetic resonance (NMR) has been used for many years as a means of chemical analysis. NMR is a type of radio frequency spectroscopy which is based upon small energy differences between electrically charged atomic nuclei which are spinning parallel or antiparallel to an applied magnetic field. When radio frequency energy is applied to the sample, these spinning atomic nuclei change spin states and in doing so, absorb some of the radio frequency energy. Nuclei in slightly different chemical environments within the same molecule change spin state at slightly different energies and this produces characteristic absorptions or resonances which help identify the molecular structure.

NMR has more recently been used in examinations of the human body. Other methods such as computerized axial tomography (CAT scanning) have been used in the past for this purpose, and still are. However, because NMR does not use ionizing radiation, it is believed to have some safety advantages over CAT. Thus, NMR is an advantageous method of producing cross-sectional images of the human body.

The quality of the images obtained from an NMR scan are based on two properties: the proton densities of the various tissues and differences in proton relaxation rates. The proton density of tissues cannot be readily altered. Proton relaxation rates can be adjusted by adding a paramagnetic relaxation agent, more commonly known as a "contrast agent." Contrast agents enhance the contrast in NMR images between magnetically similar but histologically dissimilar tissues.

Gadolinium has been tested as a contrast agent in the past because it has a large magnetic moment, which efficiently relaxes magnetic nuclei. Gadolinium's strong paramagnetic properties are the result of its seven unpaired electrons.

One drawback of gadolinium as a contrast agent is its toxicity to animals. One possible remedy for this problem is to incorporate gadolinium in a compound that would pass through the body and be excreted without releasing toxic gadolinium ions. Unfortunately, the rare earth elements, such as gadolinium, do not form stable covalent bonds with organic molecules, so such molecules can decompose in vivo and release the toxic ions. Complexes of gadolinium might overcome this problem.

There is a need for effective contrast agents which avoid the toxicity problems inherent in using gadolinium.

SUMMARY OF THE INVENTION

The present invention concerns NMR contrast agents which include a chelate of gadolinium with either 1,4,7-triazacyclononane-N,N',N''-triacetate (NOTA), 1,4,7,10-tetrazacyclododecane-N,N',N'',N''' tetracetate (DOTA), or 1,5,9-triazacyclododecane-N,N',N''-triacetate (DOTRA), or salts thereof. When the phrase "salts thereof" is used in this patent, it means that one of the acidic hydrogen ions on an acetate group has been replaced by another cation, not that an entire acetate group has been replaced. The particular juxtaposition of the nitrogen and oxygen atoms has an important effect on the chelating properties of NOTA, DOTA, and DOTRA, so removal of an entire acetate group would harm that property. Of course, upon dissolving the chelate in solution, the cation that has replace a hydrogen ion would dissociate leaving the same central ionic species.

These contrast agents can be used to enhance NMR contrast in a living subject by administering internally to the subject an effective amount of the agent. "Administering internally" is intended to include methods such as injection, ingestion, or the like which would be known to one skilled in this field.

DOTRA, DOTA, and NOTA reduce or prevent the toxic effects of the $Gd^{3+}$ cation to in vivo processes by firmly complexing with it. DOTRA and DOTA form gadolinium chelates that are especially stable, with NOTA binding somewhat less firmly, possibly due to the small size of the "hole" in NOTA's molecule.

This binding strength should result in very low biological toxicity for contrast agents in accordance with the present invention. In addition, the agents appear to have substantially better relaxation properties than some prior art agents, which will permit the use of a smaller amount of the agents to achieve the same effect.

DETAILED DESCRIPTION OF SPECIFIC EMBODIMENTS OF THE INVENTION

The following is a procedure which can be used to synthesize NOTA:

Step 1: Synthesis of N,N',N''-tri(p-toluenesulfonyl)-diethylene-triamine

A solution of p-toluenesulfonyl chloride (191 g) in ether (500 ml) was added drop by drop to a solution of diethylene triamine (38 ml) and sodium hydroxide (40 g) in water (250 ml). The mixture was stirred for one hour at room temperature. A white precipitate was formed and was collected by filtration, washed with water, and then recrystalized using methanol. (Acetonitrile could also be used). The melting point of the recrystalized precipitate was 174° to 175° C. The yield was 90%, and should always be above 70%.

Step 2: Synthesis of di(p-toluenesulfonyl)ethylene glycol

Twenty-eight ml of ethylene glycol and 100 ml of pyridine were added over a 2.5 hour period to a stirred mixture of tosyl chloride (210 g) in pyridine (225 ml), with the mixture being cooled by a water bath. After stirring for several hours, the mixture was shaken with one liter of ice water for about ten minutes and then filtered. The residue was washed with ether, dilute sulfuric acid, water, and finally ether. (Each of the washed liquids was ice cold.) The residue was then dried by vacuum pumping and recrystallized from boiling acetonitrile. The recrystallized residue, yield 75%, had a melting point of 123° to 125° C.

Step 3: Preparation of the disodiom salt of N,N',N"-tri(p-toluenesulfonyl)diethylene triamine Each part of this step was conducted under a nitrogen atmosphere. 2.65 grams of sodium metal was weighed in hexane and placed in about 75 ml of pure ethanol. The sodium-ethanol reaction is highly exothermic, and the heat helps dissolve the sodium to give sodium ethoxide. A hot slurry of 1,4,7-tritosyl-1,4,7-triazaheptane (28.3 g) from Step 1 and 150 ml of ethanol was stirred in a reaction vessel with a reflux condenser. The slurry was heated to reflux using an oil bath, and then the sodium ethoxide was added as rapidly as possible. After continued stirring and flushing with nitrogen, a white solid precipitated. Slight heating and flushing continued until all the ethanol was removed and the dry disodium salt of 1,4,7-tritosyl-1,4,7-triazaheptane was left.

Step 4: Synthesis of 1,4,7-triazacyclononane-N,N',N"-tritosylate

This step was conducted without removing the dry salt from the Step 3 reaction vessel. The dry disodium salt was dissolved in 225 ml of dry dimethyl formamide (DMF), once again under a nitrogen atmosphere. The mixture was stirred and heated to 95° to 110° C. Next, a 0.2M solution of ethylene glycolditosylate (18.5 g) in DMF was added over a period of three hours. After one additional hour of stirring at 100° C., the mixture was cooled overnight. It was then concentrated by distillation under reduced pressure until precipitation began. The concentrate was poured into 500 mls of vigorously stirred water and filtered. The residue was washed with water, dried by vacuum pumping, and recrystallized from boiling acetone. The product, 1,4,7-triazacyclononane-N,N',N"-tritosylate, had a melting point of 217° to 220° C. and was present in a yield of 70%.

Step 5: Synthesis of 1,4,7-triazacyclononane trihydrobromide

One hundred twenty ml of a mixture of 47% HBr, 67 ml of glacial acetic acid, 13.99 g of the product of Step 4 were heated to 100° C., and the volume was then remeasured. The mixture was then refluxed for fifty hours and concentrated by atmospheric distillation to about 20% of the beginning volume. The concentrate was then filtered. The residue, containing 1,4,7-triazacyclononane-N,N',N"-trihydrobromide, was extracted into water and then recovered by evaporation in vacuo. The trihydrobromide was recrystallized from boiling hydrobromic acid. Its melting point was 280° C, and it was present in 70% yield. Tosylate groups were completely absent in the NMR spectra of the trihydrobromide.

Step 6: Synthesis of 1,4,7-triazacyclononane-N,N',N"-triacetete (NOTA)

A solution of 4.72 g of bromoacetic acid and 1.2 g of sodium hydroxide in 10 ml of water was added with stirring to a solution of 3.72 g of the product of Step 5 and 1.2 g of sodium hydroxide in 3.5 ml of water at about 20° C. The mixture was heated to 85° C. with an oil bath while being stirred, and then 1.2 g of sodium hydroxide, dissolved in 6.5 ml of H₂O, was added dropwise with stirring. The temperature was maintained between 80° to 90° C. for one and one-half hours. The contents of the flask were then cooled to room temperature and the pH was adjusted to about 3.5 with concentrated hydrobromic acid. 25 ml of ethyl alcohol was added, and the solution was stirred for an hour under refrigeration. A white crystalline precipitate formed which was filtered out, washed with pure ethanol, and dried in a vacuum oven at 70° C. overnight. This product was NOTA, and the 2.5 g of it represented an at least 70% yield.

Elemental analysis showed close correspondence to what was expected for $C_{12}H_{21}O_6N_3$ $(NaBr)_3.3H_2O$. Calculated: 25.58% C, 4.79% H, 7.46% N, 28.42% Br, and 8.17% Na. Found: 25.39% C, 4.89% H, 7.43% N, 28.44% Br, and 8.00% Na.

This synthesis can be summarized as shown below.

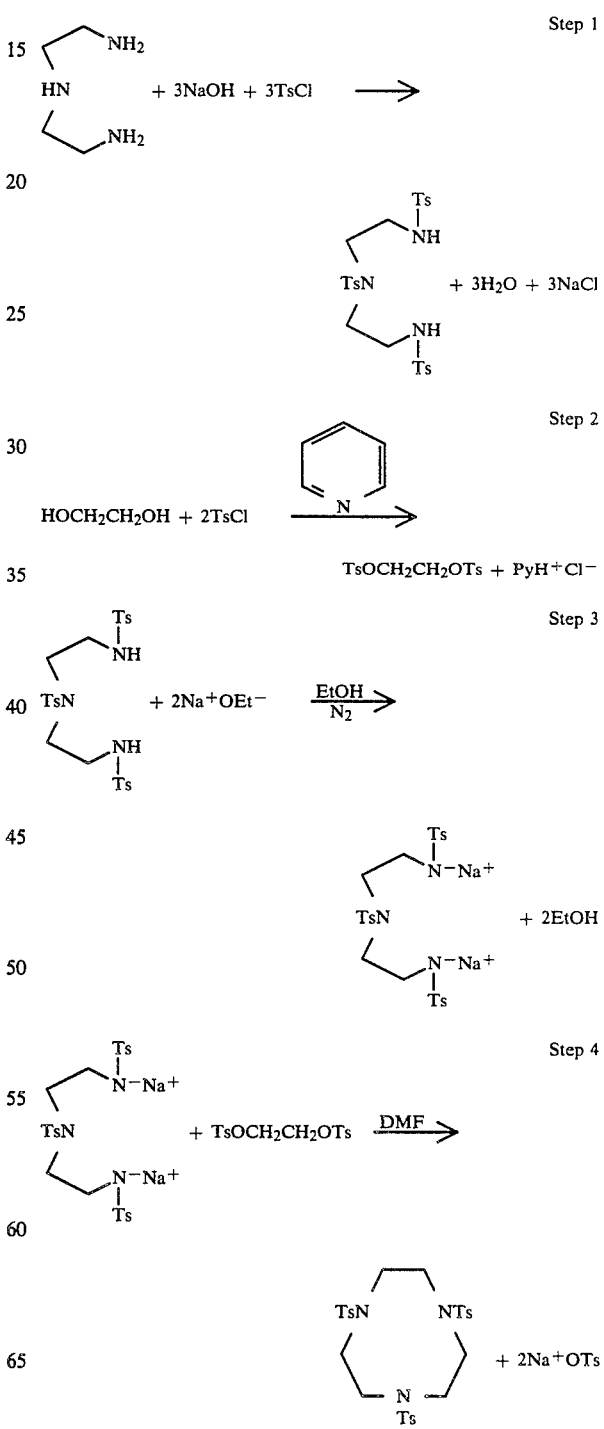

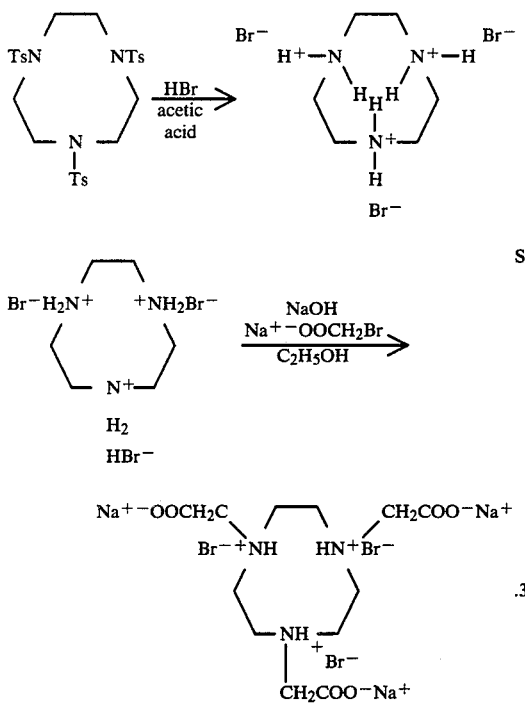

DOTA and DOTRA can be synthesized using generally the same procedure, but starting with triethylene tetraamine instead of diethylene triamine to synthesize DOTA and dipropylene triamine and 1,3 propanediol instead of diethylene triamine and ethylene glycol, respectively, for synthesizing DOTRA. The remaining reagents would be identical with only the stoichiometric quantities varying for DOTA.

Once DOTA, NOTA or DOTRA has been obtained in crystalline form, a measured amount of it is dissolved in water and an equimolar amount of a gadolinium salt, such as gadolinium chloride or gadolinium nitrate, is added to the solution. The Gd-NOTA complex forms spontaneously above pH 5 while the Gd-DOTA and Gd-DOTRA complexes are kinetically slower to form and may require heating to 80° C. for 30 minutes to increase the rate of chelation.

Salts of DOTA, NOTA and DOTRA could, of course, also be used, since the counter ions will dissociate in solution. What synthetic procedure is most convenient may dictate which salt to use. The meglumine salt of Gd-DOTA, Gd-NOTA or Gd-DOTRA is one which should be useful in contrast agent formulations.

The contrast agents could be formulated as a saline solution and packaged in bottles having a rubber septum across the opening to permit withdrawing the solution with a syringe.

Contrast agents in accordance with the present invention can be used with NMR apparatus which are well known to those skilled in this field. Examples of U.S. patents which disclose NMR apparatus are U.S. Pat. Nos. 4,374,360; 4,398,148; 4,409,550; 4,425,547; 4,442,404; and 4,450,408, all of which are incorporated herein by reference. NMR imaging should probably be done within a few hours after administering the contrast agent to the subject, since the agent should be excreted from the body fairly rapidly.

The preceding is intended to illustrate specific embodiments of the present invention, and not to be an exhaustive description of all possible embodiments. Those skilled in this field will recognize that certain modifications could be made.

I claim:

1. A method of enhancing NMR contrast in a living subject, comprising administering internally to the subject an effective amount of a contrast agent which comprises a chelate of gadolinium with a compound selected from the group consisting of DOTRA, DOTA, NOTA, and salts thereof.

2. A method of enhancing NMR contrast in a living subject, comprising administering internally to the subject an effective amount of a contrast agent which comprises a chelate of gadolinium with DOTRA or a salt thereof.

3. A method of enhancing NMR contrast in a living subject, comprising administering internally to the subject an effective amount of a contrast agent which comprises a chelate of gadolinium with DOTA or a salt thereof.

4. A method of enhancing NMR contrast in a living subject, comprising administering internally to the subject an effective amount of a contrast agent which comprises a chelate of gadolinium with NOTA or a salt thereof.

* * * * *